(12) United States Patent
Carter et al.

(10) Patent No.: US 6,860,272 B2
(45) Date of Patent: Mar. 1, 2005

(54) DEVICE FOR IMMOBILIZING A PATIENT AND COMPRESSING A PATIENT'S SKELETON, JOINTS AND SPINE DURING DIAGNOSTIC PROCEDURES USING AN MRI UNIT, CT SCAN UNIT OR X-RAY UNIT

(75) Inventors: Clayton Reed Carter, North Logan, UT (US); Gregory Jon Hicken, Logan, UT (US)

(73) Assignee: Portal, Inc., North Logan, UT (US)

( * ) Notice: Subject to any disclaimer, the term of this patent is extended or adjusted under 35 U.S.C. 154(b) by 281 days.

(21) Appl. No.: 10/051,363

(22) Filed: Jan. 17, 2002

(65) Prior Publication Data

US 2003/0131855 A1 Jul. 17, 2003

(51) Int. Cl.$^7$ .................................................. A61F 5/37
(52) U.S. Cl. ....................... 128/870; 128/869; 128/846; 5/628; 5/651
(58) Field of Search .................... 128/869, 870, 128/846, 876; 5/625, 628, 647, 624, 651

(56) References Cited

U.S. PATENT DOCUMENTS

| | | | |
|---|---|---|---|
| 3,629,581 A | * | 12/1971 | Smith .......................... 378/209 |
| 3,783,863 A | | 1/1974 | Kliever |
| 3,851,644 A | | 12/1974 | Slagle |
| 4,202,355 A | | 5/1980 | Loeffler |
| 4,282,865 A | * | 8/1981 | Pogue .......................... 601/26 |
| 4,320,749 A | * | 3/1982 | Highley ........................ 602/27 |
| 4,369,982 A | * | 1/1983 | Hein et al. ............. 280/47.131 |
| 4,407,277 A | | 10/1983 | Ellison |
| 4,580,554 A | | 4/1986 | Goodley |
| 4,669,106 A | | 5/1987 | Ammerman |
| 4,674,483 A | * | 6/1987 | Frederick ..................... 602/40 |
| 4,794,656 A | * | 1/1989 | Henley, Jr. ...................... 5/628 |
| 4,799,497 A | | 1/1989 | Riley, II |
| 4,854,305 A | | 8/1989 | Bremer |
| 4,865,022 A | * | 9/1989 | Gorsen ......................... 602/33 |
| 4,890,604 A | | 1/1990 | Nelson |
| 4,956,885 A | | 9/1990 | Alich et al. |
| 5,154,186 A | | 10/1992 | Laurin et al. |
| 5,179,746 A | * | 1/1993 | Rogers ........................... 5/625 |
| 5,201,089 A | * | 4/1993 | Ferreira ......................... 5/627 |
| 5,217,488 A | | 6/1993 | Wu |
| 5,242,351 A | * | 9/1993 | Berg et al. ................... 482/110 |
| 5,342,290 A | * | 8/1994 | Schuellein .................... 602/36 |
| 5,427,116 A | | 6/1995 | Noone |
| 5,451,232 A | | 9/1995 | Rhinehart et al. |
| 5,476,095 A | | 12/1995 | Schnall et al. |
| 5,479,471 A | * | 12/1995 | Buckland ..................... 378/208 |
| 5,549,849 A | | 8/1996 | Namura et al. |
| 5,602,809 A | | 2/1997 | Shikano |
| 5,662,597 A | | 9/1997 | Chitwood |
| 5,680,861 A | | 10/1997 | Rohling |
| 5,724,970 A | | 3/1998 | Votruba et al. |
| 5,730,706 A | | 3/1998 | Garnies |
| 5,743,264 A | | 4/1998 | Bonutti |
| 5,762,073 A | | 6/1998 | Choy |
| 5,779,733 A | * | 7/1998 | Willen et al. ................ 606/237 |
| 5,807,255 A | | 9/1998 | Yokota et al. |
| 5,810,006 A | | 9/1998 | Votruba et al. |
| 5,836,878 A | | 11/1998 | Mock et al. |

(List continued on next page.)

Primary Examiner—Henry Bennett
Assistant Examiner—Camtu Nguyen
(74) Attorney, Agent, or Firm—Workman Nydegger (57) ABSTRACT

The present invention relates to a device for use in diagnostic procedures using an MRI unit, CT Scan unit or x-ray unit, comprising a patient resting surface to which a patient's chest, shoulders, knees and lower legs are firmly, but comfortably secured, immobilizing the patient, a foot plate upon which the patient's feet rest or are secured, a pressure creating apparatus which applies a predictable, controllable and variable pressure to the patient's skeleton, joints and spine, and further immobilizes the patient who is secured to the patient resting surface and foot plate with immobilizers, an anchor securing the pressure creating apparatus to the second end of the patient resting surface.

20 Claims, 8 Drawing Sheets

U.S. PATENT DOCUMENTS

| | | | |
|---|---|---|---|
| 5,899,859 A | 5/1999 | Votruba et al. | |
| 5,991,651 A * | 11/1999 | LaBarbera | 600/415 |
| 6,000,399 A | 12/1999 | Choy | |
| 6,026,526 A * | 2/2000 | Payman | 5/602 |
| 6,217,538 B1 | 4/2001 | Anderson | |
| 6,273,867 B1 | 8/2001 | Glazer | |
| 6,295,672 B1 * | 10/2001 | Vassallo, Jr. | 5/626 |
| 6,611,703 B2 | 8/2003 | Kuth et al. | |
| 6,708,693 B1 | 3/2004 | Choy et al. | |

* cited by examiner

DEVICE FOR IMMOBILIZING A PATIENT AND COMPRESSING A PATIENT'S SKELETON, JOINTS AND SPINE DURING DIAGNOSTIC PROCEDURES USING AN MRI UNIT, CT SCAN UNIT OR X-RAY UNIT

CROSS-REFERENCES TO RELATED APPLICATIONS (None)

STATEMENT REGARDING FEDERALLY SPONSORED RESEARCH OR DEVELOPMENT (None)

REFERENCE OF A "MICROFICHE APPENDIX"

(None)

BACKGROUND

The present invention relates to a device for diagnostic purposes for use with imaging technologies such as Magnetic Resonance Imaging ("MRI") Computerized Tomography ("CT Scan") or x-rays.

Traditionally, when a patient is examined using either a conventional MRI unit or a CT Scan unit, and regularly when a patient is examined using an x-ray unit, the patient is placed in a supine, relaxed and mobile position. Such positioning of the patient compromises the effectiveness of the MRI unit, CT Scan unit and x-ray unit as diagnostic tools and causes various problems several of which are discussed below.

A significant problem for technicians operating MRIs, CT Scans and x-rays is that patients regularly move during the imaging process. Such unwanted movements cause blurred or otherwise unreadable images and, consequently, require that new images be taken each time a patient's movements cause such problems. This repetition of the diagnostic procedure doubles the amount of time required to obtain images for diagnosis. It also doubles the costs of the diagnostic procedure which causes increased costs to health care providers and ultimately increases the overall costs of health care.

Another problem encountered by technicians employing a conventional MRI unit to image a patient's hips is that the patient's feet are mobile. During imaging a patient may move his or her feet causing his or her hips to be unsuitably positioned for imaging.

Another substantial problem associated with placing patients in a relaxed and supine position during an examination of the skeleton, joints and spine using conventional MRI units, CT Scan units, or x-ray units is that the resulting diagnosis is often inaccurate. Studies have shown that the pressure placed on a patient's skeleton, joints and spine while in the relaxed supine position is significantly less than the pressures on the patient's skeleton, joints and spine while the patient is sitting, standing or walking. Therefore, when an MRI unit, CT Scan unit or x-ray unit is used to diagnose injuries and disease in a patient's skeleton, joints and spine, their effectiveness as diagnostic instruments is compromised. This occurs because the reduced pressures on the skeleton, joints and spine cannot accurately re-create the conditions existing in the skeleton, joints or spine when the patient is sitting, standing or walking. For example, conventional MRI techniques are often used in the diagnosis of lumbar disc disease or injury. Experience has shown that is not uncommon to find a disassociation between the severity of the patient's clinical symptoms and evidence of injury or disease shown through MRI imaging. This disassociation can be explained, in part, by the general inability of conventional MRI diagnosis techniques to allow the patient to be imaged while in a variety of positions, including the standing or sitting positions, to vary the intra-discal pressures and alignment of the vertebrae. The relaxed supine position, in which all conventional MRIs of the lumbar spine are performed, is associated with the lowest intra-discal pressure, and is thus not a good position to provoke disc herniation, and is thus not the optimal position for accurate disc herniation diagnosis. This same problem is experienced with the imaging and diagnosis of skeleton, joint and other spine injury or disease.

Information relevant to attempts to address the third of the above-discussed problems can be found in U.S. Pat. Nos. 6,000,399 (incorporated herein by this reference) and 5,779,733 (incorporated herein by this reference). However, each one of these references suffers from one or more of the following disadvantages: the apparatus and method is awkward to operate which may cause the incorrect use of the apparatus or the failure to use the apparatus; the apparatus and method is not sophisticated enough to predictably and controllably exert pressure on the spine; the apparatus comprises materials which compromise or affect the accuracy or operation of an MRI unit; the apparatus and method do not immobilize the patient; the apparatus and method are not made for use in CT Scan units or x-ray units.

Accordingly, it is a purpose of the present invention to provide a method and apparatus for the substantial immobilization of either a portion or substantially all of a patient's body during imaging with either a conventional MRI unit, CT Scan unit or x-ray unit.

It is a further purpose of the present invention to provide a method and apparatus for the immobilization of a patient's feet in order to maintain the patient's hips in a proper position throughout the imaging of the hips with a conventional MRI unit.

Accordingly, it is also a purpose of the present invention to provide a method and apparatus for the positioning of a patient's skeleton, joints and spine for imaging with either a conventional MRI unit, CT Scan unit, or x-ray unit which allow the skeleton, joints and spine of a patient to be readily and easily placed in an orientation which may assist in the diagnosis of injured or diseased areas of each the skeleton, joints and spine by applying substantially the same pressure on each as they would experience while the patient is sitting, standing or walking.

It is a further purpose of the present invention to provide a method and apparatus which allows a patient to be readily and easily oriented for imaging with either a conventional MRI, CT Scan, or x-ray imaging device in a manner which predictably, controllably, variably and accurately applies a pressure on the skeleton, joints, and spine of the patient during the imaging process.

It is a further purpose of the present invention to provide a method and apparatus which may be utilized in connection with either MRI, CT Scan, or x-ray imaging devices of conventional construction for enhanced imaging of a patient and which do not compromise or affect the accuracy or operation of the MRI, CT Scan and x-ray imaging devices.

Thus there are multiple problems to be solved for the examination of a patient's body, skeleton, joints and spine with MRI units, CT Scan units and x-ray units.

SUMMARY

The present invention is directed to an apparatus and method that satisfy the needs defined in the section of this patent application entitled "Background". The apparatus and method comprise an apparatus for the immobilization of a patient and compression of a patient's skeleton, joints and spine during imaging with either an MRI unit, CT Scan unit, or x-ray unit. The apparatus comprises: a patient resting surface; shoulder and chest immobilizers attached to first end of the patient resting surface; knee immobilizers attached to the second end of the patient resting surface; lower leg immobilizers attached to the second end of the patient resting surface; a pressure creating apparatus attached to the second end of the patient resting surface; and feet immobilizers attached to the pressure creating apparatus.

The patient resting surface comprises either: a connected first and second rigid panel for support and positioning of the shoulders, back and lower body of a patient to be diagnosed with either an MRI unit, CT Scan unit, or x-ray unit; or a single rigid panel for support and positioning of a supine patient to be diagnosed with either an MRI unit, CT Scan unit, or x-ray unit.

The shoulder, chest, knee, lower leg, and feet immobilizers comprise fabric straps which are attached to the patient resting surface and pressure creating apparatus and which are arranged around the shoulders, chest, knees, lower legs and feet of a supine patient, and secure the supine patient to the patient resting surface and pressure creating apparatus.

The pressure creating apparatus comprises: a first and second elastic medium (the term "elastic medium" includes, but is not limited to, shock chord, surgical tubing, and bungee chord); an anchor which attaches to the second end of the patient resting surface and supports and anchors the first and second elastic media; first and second pressure transferring plungers which transfer the pressure from the first and second elastic media; a foot plate which rests upon the first and second pressure transferring plungers and receives upward pressure therefrom.

An alternative embodiment of the pressure creating apparatus comprises: a first and second pressure resistant medium (the term "pressure resistant medium" includes, but is not limited to, coil spring and viscoelastic rod); an anchor which attaches to the second end of the patient resting surface and contains and supports the first and second pressure resistant media; first and second pressure transferring plungers which transfer the pressure from the first and second pressure resistant media; a foot plate which rests upon the first and second pressure transferring plungers and receives upward pressure therefrom.

The pressure creating apparatus comprises: an elastic medium (the term "elastic medium" includes, but is not limited to, shock chord, surgical tubing, and bungee chord); an anchor which attaches to substantially the middle part of the patient resting surface and supports and anchors the elastic medium; a foot plate which slides longitudinally along the patient resting surface and is suspended from the elastic medium and receives upward pressure therefrom.

A method for immobilizing a patient and compressing a patient's skeleton, joints and spine during imaging with either an MRI unit, CT Scan unit, and x-ray unit wherein the method comprises: placing a patient in the supine position on the patient resting surface; securing of the supine patient's shoulders and chest to the patient resting surface with the shoulder and chest immobilizers; then applying an upward force to the feet of the patient with the pressure creating apparatus; after which the patient's knee or knees are secured to the patient resting surface with the knee immobilizers; after which the patient's lower leg or legs are secured to the patient resting surface with the lower leg immobilizers; after which the patient's foot or feet are secured to the pressure creating apparatus with the feet immobilizers; whereby substantially all of the patient's body is immobilized and the patient's skeleton, joints and spine are compressed.

BRIEF DESCRIPTION OF THE SEVERAL VIEWS OF THE DRAWINGS

The present invention will now be described in detail with reference to the attached drawings, showing a preferred embodiment of the invention as well as multiple alternative embodiments, whereby.

DETAILED DESCRIPTION

Figure 1:
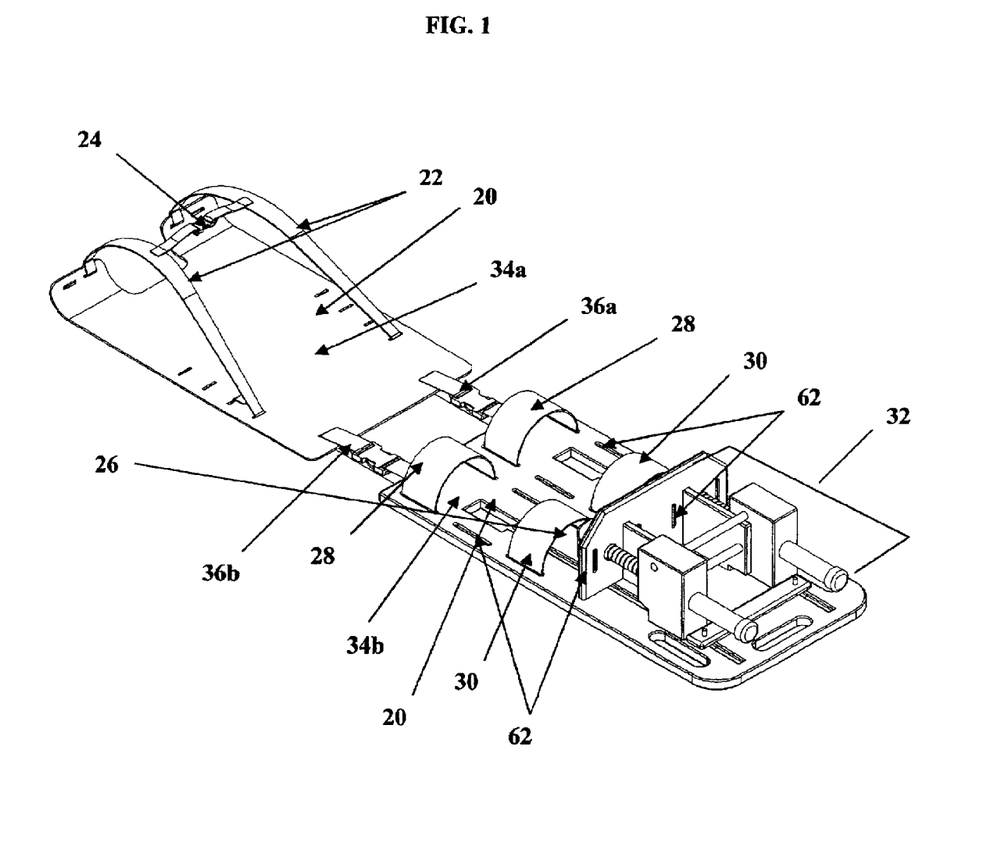
FIG. 1 is an isometric view of the preferred embodiment of the present invention.
Figure 2:
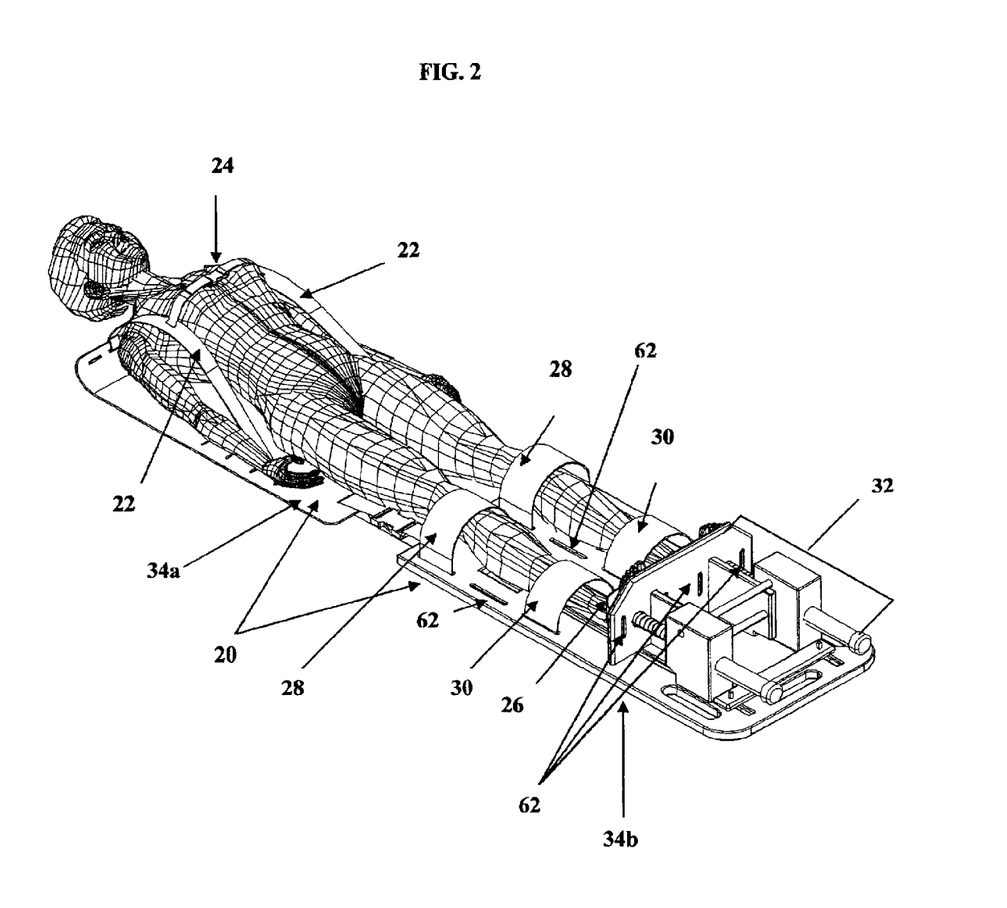
FIG. 2 is an isometric view of the preferred embodiment of the present invention showing the orientation of a patient placed thereon.

Referring to FIGS. 1, 2, 3 and 4, a patient resting surface 20 constructed in accordance with the present invention supports a patient in the supine position as shown in FIG. 2. Attached to the first end of the patient resting surface are shoulder immobilizers 22 and a chest immobilizer 24 to secure the patient's shoulders and chest to the patient resting surface as shown in FIG. 2. Attached to the second end of the patient resting surface are, knee immobilizers 28 and lower leg immobilizers 30 to secure the patient's knees and lower legs to the patient resting surface. Attached to the second end of the patient resting surface is a pressure creating apparatus 32 which exerts an upward pressure on the patient who is secured to the patient resting surface as shown in FIG. 2.

The invention will now be described in detail with reference to the attached drawings showing preferred and alternative embodiments of the present invention.

Figure 3:
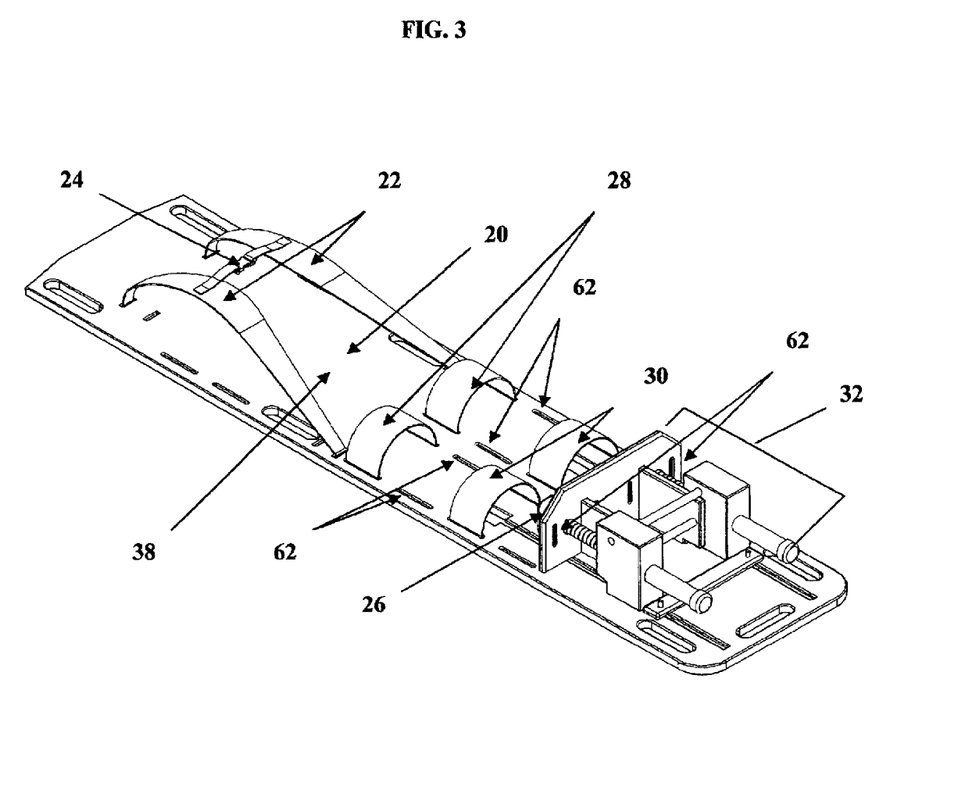
FIG. 3 is an isometric view of an alternative embodiment of the present invention comprising alternative embodiments of the patient resting surface and pressure creating apparatus.
Figure 4:
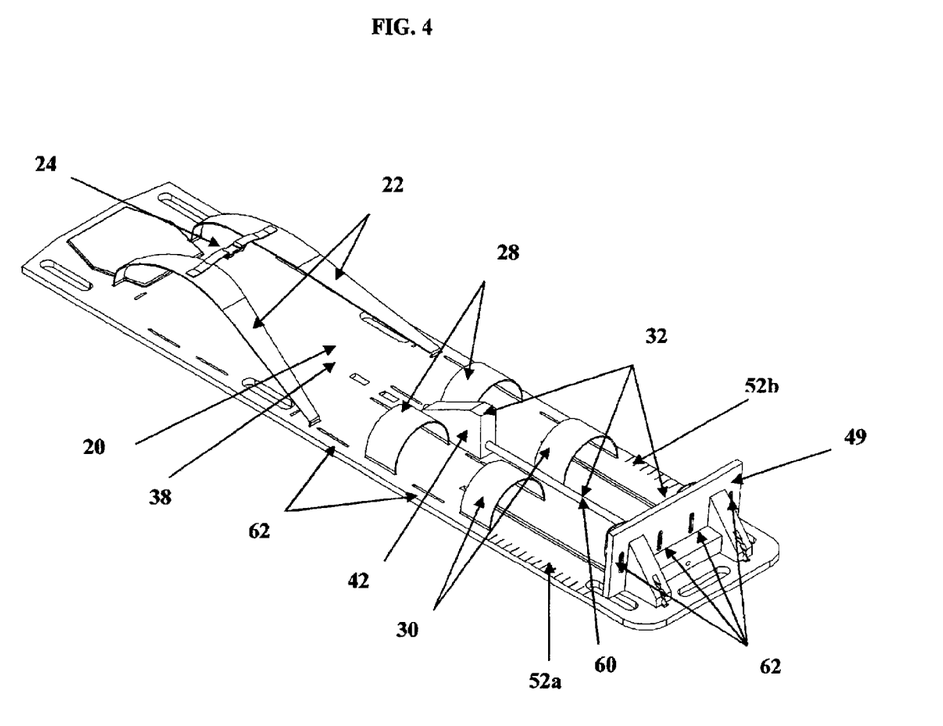
FIG. 4 is an isometric view of a second alternative embodiment of the present invention comprising an alternative embodiment of the patient resting surface and pressure creating apparatus.
Figure 5:
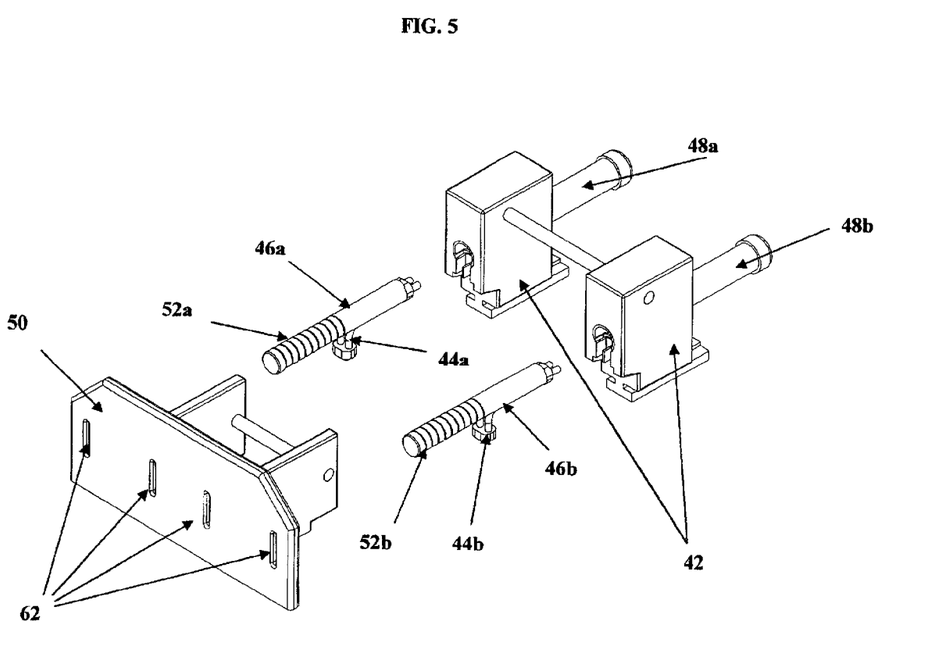
FIG. 5 is an exploded isometric view of the preferred embodiment of the pressure creating apparatus comprising elastic media.

The present invention comprises a patient resting surface 20 as shown in FIGS. 1, 3 and 4. The preferred embodiment of the patient resting surface comprises a first and second rigid panel 34a, 34b connected to each other with a first and second connector 36a, 36b as shown in FIG. 1. While the preferred embodiment of the patient resting surface comprises two separate panels as shown in FIG. 1, other alternative embodiments may be employed, such as a single rigid panel 38 as shown in FIGS. 3 and 4. The primary requirements of the patient resting surface are that it is of sufficiently rigid construction to withstand the pressures placed upon it and is constructed of materials which do not affect, compromise or distort the imaging processes of the MRI, CT Scan or x-ray and are otherwise suitable for use with an MRI, CT Scan, and x-ray.

The MRI, CT Scan and x-ray are well-known diagnostic units and are not the subject of the present invention and thus will not be described in greater detail.

Figure 6:
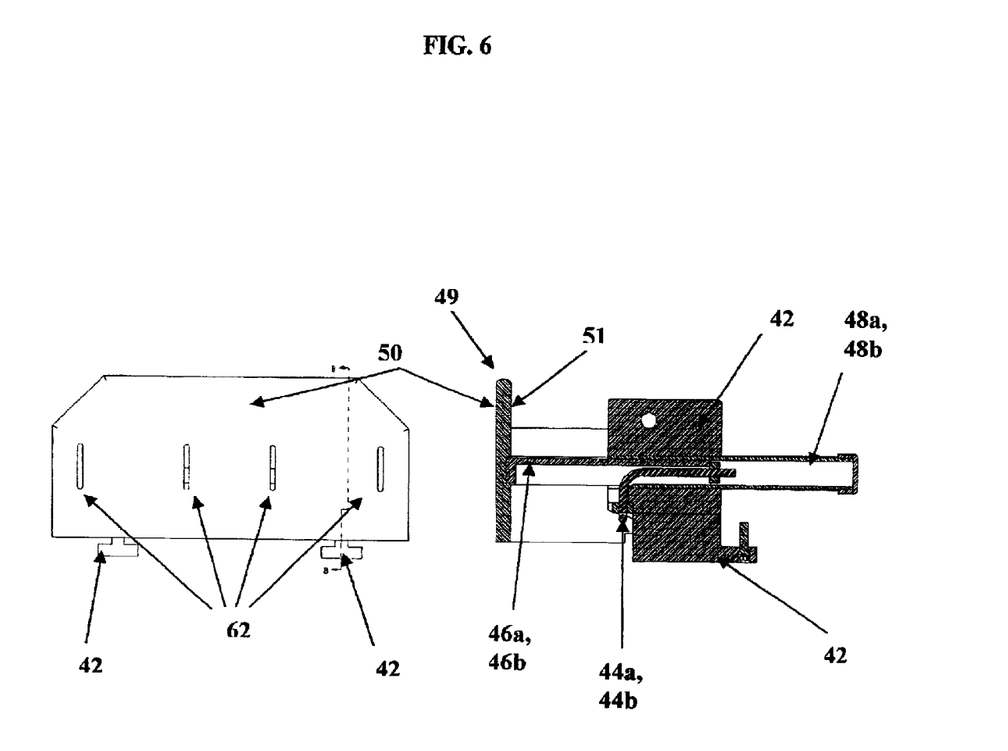
FIG. 6 is a cross sectional side view of the preferred embodiment of the pressure creating apparatus comprising elastic media.
Figure 7:
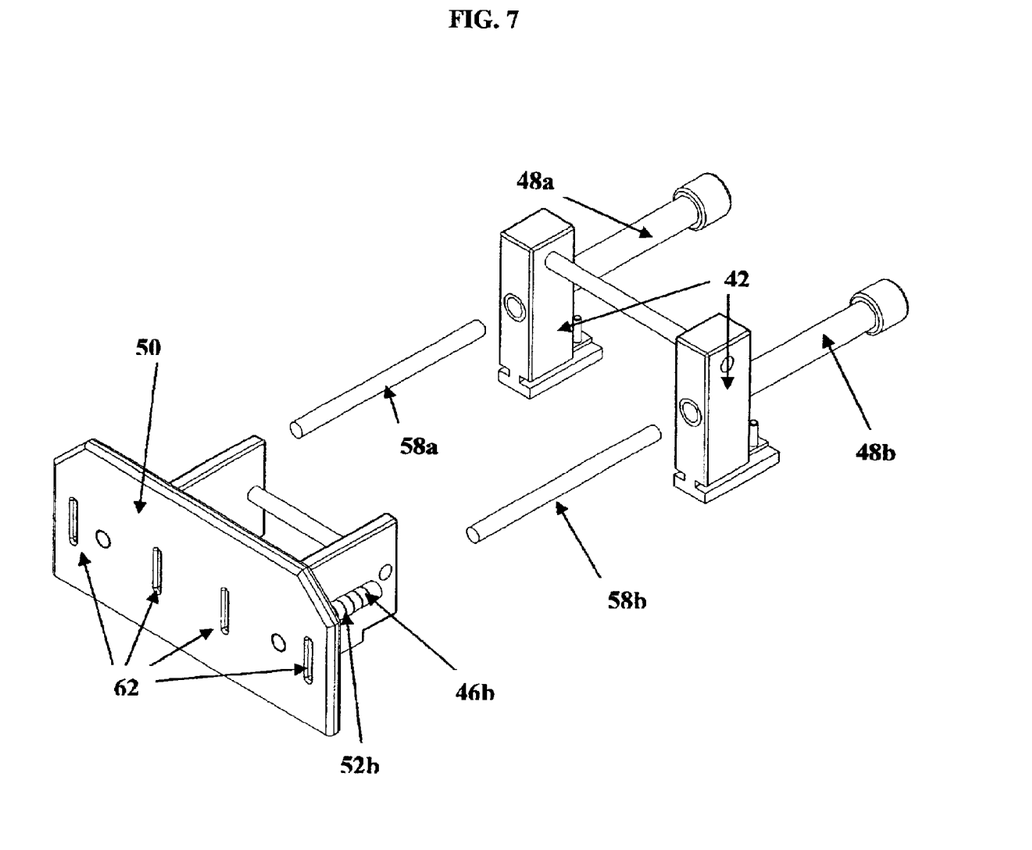
FIG. 7 is an exploded isometric view of an alternative embodiment of the pressure creating apparatus comprising pressure resistant media.
Figure 8:
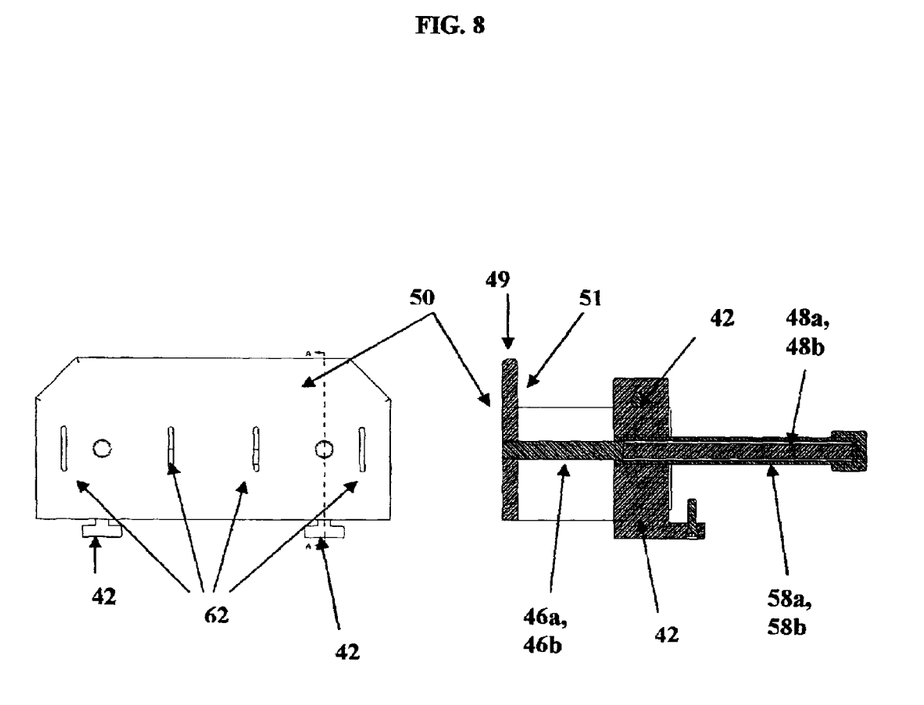
FIG. 8. is a cross sectional side view of an alternative embodiment of the pressure creating apparatus comprising pressure resistant media.

The present invention also comprises a pressure creating apparatus. Referring to FIGS. 1, 2, 5 and 6, the preferred embodiment of such pressure creating apparatus 32, comprises an adjustable anchor 42 which attaches to the second end of the patient resting surface. A first and second elastic medium 44a, 44b (the term "elastic medium" includes, but is not limited to, shock chord, surgical tubing, and bungee chord) are each attached at one end to the adjustable anchor 42 and attached at the opposite end of each elastic medium to a corresponding first and second pressure transferring plunger 46a, 46b. The first and second pressure transferring plungers 46a, 46b each fit into a corresponding first and second cylinder 48a, 48b within the adjustable anchor 42 and travel longitudinally inside the corresponding first and second cylinders 48a, 48b. Such first and second pressure transferring plungers 46a, 46b are attached to the adjustable anchor 42 by means of the corresponding first and second elastic media 44a, 44b as shown in FIG. 6. The first and second pressure transferring plungers 46a, 46b support the second side of an adjustable foot plate 51. The first side of the adjustable foot plate 50 supports the foot or feet of a patient as shown in FIG. 2. The patient presses downward on the first side of the adjustable foot plate 50 which motion downwardly depresses the first and second pressure transferring plungers 46a, 46b into the corresponding first and second cylinders 48a, 48b within the adjustable anchor 42. Such downward depression of the first and second pressure transferring plungers 46a, 46b stretches the corresponding first and second elastic media 44a, 44b thereby creating an upward pressure and transferring such upward pressure to the corresponding first and second pressure transferring plungers 46a, 46b which transfer the upward pressure to the second side of the adjustable foot plate 51 which in turn transfers the upward pressure to the foot or feet of the patient. The upward pressure created by the pressure creating apparatus 32 is measured by the length of the first and second pressure transferring plungers 46a, 46b remaining visible above the adjustable anchor 42. Such length is indicated by first and second integrated pressure scales 52a, 52b shown on each corresponding first and second pressure transferring plunger 46a, 46b. While the above-description describes the preferred embodiment of the pressure creating apparatus, alternative embodiments of the pressure creating apparatus may be employed to create the necessary pressure.

Referring to FIGS. 1, 2, 7 and 8, an alternative embodiment of the pressure creating apparatus 32 comprises an adjustable anchor 42 which attaches to the patient resting surface. A first and second force resistant medium 58a, 58b (the term "force resistant medium" includes, but is not limited to, coil springs and viscoelastic rods) rest inside corresponding first and second cylinders 48a, 48b within the adjustable anchor 42. A corresponding first and second pressure transferring plunger 46a, 46b each fit into the corresponding first and second cylinders 48a, 48b within the adjustable anchor 42. One end of the first and second pressure transferring plungers 46a, 46b are connected to the second side of an adjustable foot plate 51 and the opposite end of each fit into the corresponding first and second cylinders 48a, 48b, resting upon the corresponding first and second force resistant media 58a, 58b. The first and second pressure transferring plungers 46a, 46b are attached to the second side of the adjustable foot plate 51 while the first side of the adjustable foot plate 50 supports the foot or feet of a patient. The patient presses downward on the first side of the adjustable foot plate 50 which in turn downwardly depresses the first and second pressure transferring plungers 46a, 46b into the corresponding first and second cylinders 48a, 48b within the adjustable anchor 42. Such downward depression of the first and second pressure transferring plungers 46a, 46b compresses the corresponding first and second force resistant media 58a, 58b which in turn exert an upward pressure on the corresponding first and second pressure transferring plungers 46a, 46b which transfer the upward pressure to the second side of the adjustable foot plate 51 which in turn transfers the upward pressure to the foot or feet of the patient. The upward pressure created by the pressure creating apparatus 32 is measured by the length of the first and second pressure transferring plungers 46a, 46b remaining visible above the adjustable anchor 42. Such length is indicated by first and second integrated pressure scales 52a, 52b shown on each corresponding first and second pressure transferring plunger.

Another alternative embodiment of the pressure creating apparatus 32 comprises an adjustable anchor 42 which is attached to the patient resting surface as shown in FIG. 4. An elastic medium 60 (the term "elastic medium" includes, but is not limited to, shock chord, surgical tubing, and bungee chord) is attached at one of its ends to the adjustable anchor 42 and at its opposite end to the center of the adjustable foot plate 49 which supports the foot or feet of a patient. The patient presses downward on the adjustable foot plate 49 which stretches the elastic medium 60, exerting an upward pressure on the foot or feet of the patient. The upward pressure created by the pressure creating apparatus 32 is indicated by the position of the adjustable foot plate 49 on the patient resting surface 20. Such position is indicated by a first and second integrated pressure scale 52a, 52b shown on the second end of the patient resting surface.

While the above-descriptions describe multiple alternative embodiments of the pressure creating apparatus 32, other alternative constructions or configurations of the pressure creating apparatus may be employed to create the necessary pressure.

All of the elements of the present invention are of sufficiently rigid construction to withstand the pressures placed upon them and are constructed of materials which will not affect, compromise or distort the imaging processes of the MRI, CT Scan, or X-ray.

Referring to FIGS. 1, 2, 3 and 4, in order to use the immobilization features of the present invention a patient is placed on the patient resting surface 20 in the supine position with his/her knee or knees bent. The shoulder and chest immobilizers 22, 24 are arranged around the shoulders and chest respectively. As the shoulders and chest of the patient are secured to the patient resting surface 20 a lumbar support cushion conforms to and supports the patient's spine. Once the patient's shoulders and chest are firmly, but comfortably secured to the patient resting surface 20 and the patient's leg or legs are fully extended, the patient's knee(s) and lower leg(s) are secured to the patient resting surface 20 with the respective knee immobilizers 28, and lower leg immobilizers 30 each of which pass through separate immobilizer slots 62 located in the patient resting surface 20. If the desired immobilization is realized, the patient is then introduced into the MRI unit, CT Scan unit or x-ray unit. However, if additional immobilization of the patient is desired, the knee immobilizers 28, and lower leg immobilizers 30 are removed from the patient's respective knee(s) and lower leg(s). Once such immobilizers are removed the pressure creating apparatus 32 is introduced and adjusted to accommodate the height of the patient after which the patient presses downward on the adjustable foot plate 49 by extending his/her leg or legs until the desired immobilization is obtained. Once such immobilization has been achieved, and the patient's leg or legs are fully extended, the patient's knee(s) and lower leg(s) are again secured to the patient resting surface 20 with the respective knee immobilizers 28, and lower leg immobilizers 30 each of which pass through separate immobilizer slots 62 located in the patient resting surface 20. Additionally, if immobilization of the patient's feet is desired, the patient's feet are firmly, but comfortably secured to the adjustable foot plate using the feet immobilizers 26 each of which pass through separate immobilizer slots 62 in the adjustable foot plate 49 as shown in FIG. 2. The patient is then introduced into the MRI unit, CT Scan unit or x-ray unit.

Referring to FIGS. 1, 2, 3 and 4, in order to use the compression feature of the present invention a patient is placed on the patient resting surface 20 in the supine position with his/her knee or knees bent. The adjustable anchor 42 and adjustable foot plate 49 are adjusted to accommodate the height of the patient. The patient's shoulders and chest are secured snugly, but comfortably to the patient resting surface 20 with shoulder and chest immobilizers 22, 24. As the shoulders and chest of the patient are secured to the patient resting surface 20 a lumbar support cushion conforms to and supports the patient's spine. Once the patient's shoulders and chest are securely, but comfortably secured to the patient resting surface 20 the position of the adjustable foot plate 49 may be further adjusted as required to provide the appropriate positioning thereof. Once such adjustment is completed the patient presses downward on the adjustable foot plate 49 by straightening or extending his/her leg or legs upon receipt of the instruction to do so. As the patient extends his/her leg or legs his/her foot or feet press downward against the adjustable foot plate 49 which in turn causes the pressure creating apparatus 32 to exert an upward pressure against the adjustable foot plate 49 which in turn transfers the upward pressure to the foot or feet of the patient. With the upward pressure from the pressure creating apparatus 32 being upwardly applied to the foot or feet of the patient and simultaneously opposed by the shoulder and chest immobilizers 22, 24 which secure the patient to the patient resting surface 20, the skeleton, joints and spine of the patient are compressed. Such compression is controllable and variable through adjustment to the adjustable anchor 42 and can be varied to recreate the compression exerted on the skeleton, joints and spine of a patient while sitting, standing or walking. The first and second integrated pressure scales 52a, 52b show when the desired compression has been reached. When the desired compression has been achieved, and the patient's leg or legs are fully extended, in order to precisely maintain the desired pressure the patient's knee(s) and lower leg(s) are secured to the second end of the patient resting surface 20 with the respective knee immobilizers 28, and lower leg immobilizers 30 each of which pass through corresponding immobilizer slots 62 located in the patient resting surface 20. The patient is then introduced into the MRI unit, CT Scan unit or x-ray unit.

The present invention has many advantages including the following. Its various immobilizers enable the substantial immobilization of either part or all of a patient's body during imaging with an MRI unit, CT Scan unit or x-ray unit. In addition to the immobilizers a patient's body may further be immobilized by compressing the patient's skeleton, joints and spine through the application of pressure from the pressure creating apparatus. The immobilizers acting separately or together with the pressure creating apparatus serve as an effective immobilization device. As discussed in the section of the patent application entitled "Background", patient movement is a significant problem during imaging with MRI units, CT Scan units and x-ray units. The above-described immobilization prevents such movements and thus allows images for diagnosis with MRI units, CT Scan units, and x-ray units to be obtained more efficiently and will also decrease the costs to health care providers and ultimately will decrease the overall costs of health care.

As discussed in the section of the patent application entitled "Background", an awkward design may cause a device to be used improperly and is not conducive to continuous use. A substantial advantage of the present invention is that it is easy to use and is conducive to continuous use.

As discussed in the section of the patent application entitled "Background", existing devices are only intended to be used with an MRI unit. A significant advantage of the present invention is that its design is conducive to use not only with an MRI unit but also with a CT Scan unit and x-ray unit of conventional construction.

As discussed in the section of the patent application entitled "Background", an unsophisticated design produces a device that is incapable of exerting a predictable and controllable pressure. A significant advantage of the present invention is that its pressure creating apparatus together with integrated pressure scales are sufficiently sophisticated to consistently exert a predictable, controllable and variable pressure on a patient's skeleton, joints and spine.

As discussed in the section of the patent application entitled "Background", a device to be used with an MRI should be constructed of materials which do not compromise or affect the accuracy or operation of an MRI. A significant advantage of the present invention is that it is constructed of materials which do not compromise or affect the accuracy or operation of an MRI.

Although the present invention has been described in considerable detail with reference to certain versions thereof, other versions are possible. Applicant intends to encompass within the language any structure presently existing or developed in the future that performs the same function as the present invention. Therefore, the spirit and scope of the claims should not be limited to the description of the preferred version contained herein.

The reader's attention is directed to all papers and documents which are filed concurrently with this specification and which are open to public inspection with this specification, and the contents of all such papers and documents are incorporated herein by reference. All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or "step for" performing a specified function, is not to be interpreted as a "means" or "step" clause as specified in 35 U.S.C. §112, ¶6.

What is claimed is:

1. An apparatus for compressing at least a portion of a patient's skeleton, joints and/or spine during imaging, the apparatus comprising:
   a first base member;
   a pair of flexible shoulder straps connected to the first base member and adapted to bear against the shoulders of the patient;
   a resilient member mounted to the first base member, the resilient member being resiliently compressible or resiliently stretchable; and
   a foot plate coupled with the resilient member such that the foot plate can be selectively moved relative to the first base member to resiliently compress or resiliently stretch the resilient member, the foot plate being adapted to receive the feet of the patient when the flexible shoulder straps bear against the shoulders of the patient.

2. The apparatus as recited in claim 1, further comprising a chest strap extending between the pair of flexible shoulder straps.

3. The apparatus as recited in claim 1, further comprising a second base member connected to the first base member, the shoulder straps being connected to the second base member while the foot plate is disposed on the first base member.

4. The apparatus as recited in claim 3, wherein the first base member is connected to the second base member by at least one flexible strap.

5. The apparatus as recited in claim 3, wherein the first base member and the second base member each comprise a substantially flat panel.

6. The apparatus as recited in claim 1, wherein the pair of flexible shoulder straps can be selectively positioned on the first base member to selectively increase or decrease the length of the straps.

7. The apparatus as recited in claim 1, wherein the pair of flexible shoulder straps can be selectively positioned on the first base member to selectively increase or decrease the distance between the pair of shoulder straps.

8. The apparatus as recited in claim 1, wherein the first base member comprises a first panel and a second panel connected to the first panel, the shoulder straps being connected to the second panel while the foot plate is disposed on the first panel.

9. The apparatus as recited in claim 1, wherein the resilient member comprises an elastic medium.

10. The apparatus as recited in claim 9, wherein the elastic medium comprises shock cord, surgical tubing, or bungee cord.

11. The apparatus as recited in claim 1, wherein the resilient member comprises a force resistant medium.

12. The apparatus as recited in claim 11, wherein the force resistant medium comprises a coil spring or a viscoeleastic rod.

13. The apparatus as recited in claim 1, further comprising an anchor member mounted to the base, the resilient member extending between the foot plate and the anchor member.

14. The apparatus as recited in claim 13, wherein the anchor member is mounted to the base member so that the anchor member can be selectively moved along the length of the base member.

15. The apparatus as recited in claim 13, wherein the anchor member is slidably coupled to the base member.

16. The apparatus as recited in claim 13, further comprising a pressure transfer member connected to the foot plate and to an end of the resilient member.

17. The apparatus as recited in claim 16, wherein the anchor member comprises a cylinder, at least a portion of the resilient member and at least a portion of the pressure transfer member being disposed in the cylinder.

18. The apparatus as recited in claim 16, wherein the pressure transfer member comprises pressure markings to indicate the level of pressure applied to the foot plate.

19. The apparatus as recited in claim 1, further comprising a leg immobilizer connected to the base member.

20. The apparatus as recited in claim 1, further comprising a foot immobilizer connected to the foot plate.

* * * * *